US008753675B1

(12) United States Patent
Chopra

(10) Patent No.: US 8,753,675 B1
(45) Date of Patent: *Jun. 17, 2014

(54) REDUCED FORM OF COENZYME Q IN HIGH BIOAVAILABILITY STABLE DOSAGE FORMS AND RELATED APPLICATIONS

(76) Inventor: Raj K. Chopra, Westbury, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/637,559

(22) Filed: Aug. 11, 2000

Related U.S. Application Data

(63) Continuation-in-part of application No. 09/488,332, filed on Jan. 20, 2000, now Pat. No. 6,740,338.

(51) Int. Cl.
*A61K 9/48* (2006.01)
*A61K 9/00* (2006.01)
*A61K 9/14* (2006.01)

(52) U.S. Cl.
USPC ............ 424/451; 424/400; 424/464; 424/489

(58) Field of Classification Search
USPC ......... 424/456, 451, 455, 464, 401, 422, 436, 424/49, 435; 514/904, 966, 969, 901, 720
See application file for complete search history.

(56) References Cited

U.S. PATENT DOCUMENTS

| | | | | |
|---|---|---|---|---|
| 4,599,232 | A | | 7/1986 | Bertelli |
| 4,602,039 | A | | 7/1986 | Cavazza |
| 4,869,900 | A | * | 9/1989 | Pozzi et al. .................. 424/94.1 |
| 4,929,437 | A | * | 5/1990 | Tobert .......................... 424/94.1 |
| 4,933,165 | A | | 6/1990 | Brown |
| 5,082,650 | A | | 1/1992 | Folkers et al. |
| 5,312,819 | A | * | 5/1994 | Fischer et al. ................. 514/220 |
| 5,316,765 | A | | 5/1994 | Folkers et al. |
| 5,409,693 | A | | 4/1995 | Perricone |
| 5,434,183 | A | * | 7/1995 | Larsson-Backström ...... 514/549 |
| 5,866,537 | A | * | 2/1999 | Bianchi ............................. 514/2 |
| 5,895,652 | A | * | 4/1999 | Giampapa ................ 424/195.17 |
| 5,908,613 | A | * | 6/1999 | Bozzacco ....................... 424/50 |
| 6,045,826 | A | | 4/2000 | Borowy-Borowski et al. |
| 6,056,971 | A | * | 5/2000 | Goldman ...................... 424/439 |
| 6,066,327 | A | * | 5/2000 | Gubernick et al. ........... 424/401 |
| 6,126,943 | A | * | 10/2000 | Cheruvanky et al. ...... 424/195.1 |
| 6,156,802 | A | * | 12/2000 | Mae et al. ..................... 514/690 |
| 6,184,255 | B1 | * | 2/2001 | Mae et al. ..................... 514/720 |
| 6,207,137 | B1 | * | 3/2001 | Shuch et al. .................... 424/49 |
| 6,300,377 | B1 | * | 10/2001 | Chopra ......................... 514/715 |
| 6,441,050 | B1 | * | 8/2002 | Chopra ......................... 514/675 |
| 6,805,880 | B1 | * | 10/2004 | Højgaard et al. ............. 424/468 |
| 6,998,501 | B1 | * | 2/2006 | Wright et al. ..................... 560/5 |

FOREIGN PATENT DOCUMENTS

| | | |
|---|---|---|
| EP | 0 383 432 | 8/1990 |
| EP | 0 882 450 | 12/1998 |
| EP | 882 450 | * 12/1998 |
| EP | 0 956 854 | 11/1999 |
| WO | WO 98/03170 | 1/1998 |

OTHER PUBLICATIONS

Bargossi et at Exogenous CoQ(10) supplementation prevents plasma ubiquinone reduction induced by HMG-CoA reductase inhibitors Molecular Aspects of Medicine 15(S):187-193 1994.*
Andrée et al. "An Endogenous Lipid-Soluble Antioxidant in Animal Tissues", in *Biological Systems*, edited by *Gilbert and Colton*. Kluwer Academic / Pienum Publishers, New York, p. 453-477, 1999.
A F. Wagner and K. Folkers. "Quasivitamins", p. 421-455.
"Cardiology" edited by J. Dereck Jeffers and Fulvio Bruno: McGraw-Hill International Ltd., England. Chapter 46 and 48, 1999.
Kagan et al. "Focus on Cellular Biochemistry", *Protoplasma*, 214: 11-18, 2000.
Singh et al. "Randomized, Double-Blind Placebo-Controlled Trial of Coenzyme Q10 in Chronic Renal Failure: Discovery of a New Role", *Journal of Nutritional & Environmental Medicine*, 10: 281-288, 2000.
Resch et al. "A Randomized Controlled Study of Reviewer Bias Against an Unconventional Therapy", *Journal of the Royal Society Medicine*, 93: 164-167, 2000.
Bliznakov, Emile G. "The Lancet", *Reprinted from the LancetU*, 356 (9240): p. 1522, 2000.
Swinyard E. Pharmaceutical Necessities Remington's Pharmaceutical Sciences (15) 67:1221 (1975).
Wagner et al. "A Non-Oxidisable Pool of Ubiquinol is Present in Animal and Plant Mitochondria. A ProtectionAgainst Free Radical Damage?" Abstract from http://www.ebec2000.com/abstracts/122.htm, 2001.

* cited by examiner

*Primary Examiner* — Susan Tran
(74) *Attorney, Agent, or Firm* — Henry D. Coleman; R. Neil Sudol

(57) ABSTRACT

The present invention relates to a reduced form of Coenzyme Q also known as ubiquinol in oral dosage form such as a gelatin capsule, preferably a soft gelatin capsule. Compositions according to the present invention include storage stable compositions comprising effective amounts of ubiquinol in combination with an amount of a reducing agent effective to maintain ubiquinol in its reduced state when formulated in capsules, tablets and other orally administrable form. Methods of using these compositions in the treatment of a number of disease states or conditions are also disclosed.

50 Claims, No Drawings

REDUCED FORM OF COENZYME Q IN HIGH BIOAVAILABILITY STABLE DOSAGE FORMS AND RELATED APPLICATIONS

This application is a continuation-in-part application of Ser. No. 09/488,332, filed Jan. 20, 2000, now U.S. Pat. No. 6,740,338, issued May 25, 2004.

FIELD OF THE INVENTION

The present invention relates to a reduced form of Coenzyme Q also known as Ubiquinol in a gelatin capsule, preferably a soft gelatin capsule, in oral administrable form as well as other forms. Compositions according to the present invention exhibit unexpectedly high bioavailability of the reduced (active antioxidant) form of Coenzyme Q. These compositions can be used to treat numerous conditions or disease states including, for example, those conditions or disease states which are associated with oxidative tissue damage or mitochondrial dysfunction, including reduced mitochondrial oxidative function, mitochondrial encephalomyolopathies, cardiomyopathies, heart disease, especially including congestive heart failure, ischemia/reperfusion tissue damage, neurodegenerative disorders, including Alzheimer's disease, dementia and Parkinson's disease, high blood pressure, periodontal disease, a weakened immune system and high cholesterol or high triglycerides, among numerous others. In fact, the compositions can be used to treat any disease state or condition in which coenzyme $Q_{10}$ is used but is less than ideally suited because of its low bioavailability.

BACKGROUND OF THE INVENTION

The use of dietary supplements has become an increasingly common approach to obtaining and maintaining good-health. One of these dietary supplements, Coenzyme Q, is a vitamin-like substance which is used to treat congestive heart failure and other cardiac problems. Coenzyme Q is the best known of a group of lipophilic quinones which have the capacity to transfer reducing equivalents or electrons within a lipid phase of cellular membranes. Other quinones of this general lipophilic type found in cells are of diverse species. A few include, for example, rhodoquinone, menaquinone, plastoquinone, chlorobiumquinone, thermoplasmaquinone and phylloquinone. See, Collins, 1985, *Methods in Micobiol.* 18: 329-36'0. It is postulated that the diene dione chemical structure of these compounds provides a platform for the transfer of one or two electrons and associated protons within the lipid bilayers of cells or to and from hydrophobic redox centers in proteins.

Reduced benzoquinones in general are effective reductants for oxygen or lipid radicals. Early studies showed that reduced coenzyme Q is an effective antioxidant. See, Mellors and Tappel, 1996, *J. Biol. Chem.*, 241: 4353-4356. Reduced coenzyme Q now appears to function as part of a complex chain of antioxidant activity. The most important role of coenzyme Q can be in reduction of radicals of α-tocopherol and ascorbate formed when these antioxidants are oxidized by oxygen or carboxyl radicals. There are no enzymes for direct reduction of tocopheryl radical or external ascorbate radical, but there are enzymes in all membranes which can reduce coenzyme Q and the reduced coenzyme Q can reduce the tocopheryl or ascorbate radicals to restore tocopherol or ascorbate. Without the support of enzymes to reduce coenzyme Q, the reduced coenzyme Q would not be a very effective antioxidant because the semiquinone formed by interaction with lipid or oxygen radicals is readily autooxidized with formation of a superoxide radical.

The enzymes involved in coenzyme Q reduction are the primary dehydrogenases for succinate. NADH or other substrates in mitochondria, the NADH cytochorome $b_5$ reductase in endo and plasma membranes and DT diaphorase or NADPH dehydrogenase enzymes primarily located in the cytosol. Villalbe, et al., *Proc. Natl. Acad. Sci.* 92:4887-4891 (1995); Beyer, et al., *Molec. Aspects Med.,* 18(S): 15-23 (1997); and Kishi, et al., *Molec. Aspects Med.,* 18(S): 71-77 (1997).

Coenzyme Q in endo membranes or plasma membranes is extensively in the reduced form, most of the coenzyme Q in total rat and human tissue is in the reduced form and most of the coenzyme Q in serum is in the reduced state. See, Takahashi, et al., *Lipids,* 28: 803-809, (1993); Åberg, et al., *Arch. Biochem. Biophys.,* 295: 230-234 (1992); and Yamamoto and Yamashita, *Molec. Aspects Med.,* 18 (S) (1997).

Studies performed to date have not focused on the differential uptake and bioavailability of one form of coenzyme Q versus another form of coenzyme Q. Nor has the art recognized the desirability of using ubiquinol as an active pharmacological agent to enhance the bioavailability of coenzyme Q from oral and other formulations.

OBJECTS OF THE INVENTION

It is an object of the invention to provide storage stable compositions for administering a reduced form of coenzyme Q.

It is an additional object of the invention to provide a method for enhancing the bioavailability of coenzyme Q to patients by administering effective amounts of coenzyme Q in a reduced form.

It is also an object of the present invention to provide an economical means for making ubiquinol-containing compositions from the more readily available and economical coenzyme $Q_{10}$ (Ubiquinone).

It is an additional object of the invention to provide methods of treating or reducing the effects of a number of disease states or conditions.

It is yet another object of the invention to provide compositions which contain ubiquinol, a reducing agent and optionally, a therapeutic reducing agent in order to provide effective compositions for the prevention and treatment of a number of disease states, conditions or ailments.

One or more of these and/or other objects of the present invention may be readily gleaned from the detailed description of the invention which follows.

SUMMARY OF THE INVENTION

The present invention relates to novel storage stable compositions in dietary supplement, cosmetic or pharmaceutical dosage form (preferably oral dosage form) comprising effective amounts of ubiquinol, a reduced form of coenzyme Q, in combination with an amount of a lipid soluble reducing agent effective to maintain ubiquinol in its reduced state when preferably formulated in a soft gelatin capsule. Compositions according to the present invention may be used for treatment of heart ailments and diseases such as congestive heart failure, high blood pressure, mitochochondrial disorders, including mitochondrial encephalomyopathy, anoxia, lactic acidosis, strokelike symptoms, neurodegenerative diseases, Kearns-Sayre syndrome and Alper's disease. Compositions according to the present invention may also be used to deter and/or treat periodontal disease, as well as lower elevated cholesterol levels in patients and to strengthen a weakened immune system as well as regulate (generally by reducing) the triglycerides in the blood. In addition, the use of ubiquinol to aid in the prevention of reperfusion injury of the heart is another potential use of the present invention. Compositions according to the present invention may optionally comprise an effective amount of a therapeutic reducing agent or other therapeutic agent which acts to enhance the effects of ubiquinol (in some cases, synergistically) in treating or reducing the effects of a disease state, condition or ailment. Methods of treating or reducing the effects of a disease state, condition or ailment using the compositions according to the present invention are also contemplated by the present invention.

Preferred therapeutic agents for inclusion in compositions according to the present invention may include, for example, HMG CoA reductase inhibitors such as the statin drugs, for example, lovastatin, pravastatin, fluvastatin, simvastatin, mevastatin, fluindostatin, atorvastatin, cerivastatin, compactin among others, for their cholesterol lowering and triglyceride regulating effects, L-carnitine, acetyl L-carnitine and propionyl L-carnitine; alpha lipoic acid (thioctic acid) or reduced alpha lipoic acid; omega-3 fatty acids, tocotrienols and tocopherols. Whereas the statin drugs are included in compositions according to the present invention to produce down regulation of cholesterol and triglyceride levels, the combination of ubiquinol and the statin drugs are particularly effective for benefitting heart patients especially those with ischemia, ischemic or dilated cardiomyopathy, or those patients at risk for suffering a first or subsequent heart attack or who are at risk of having a stroke. Compositions which comprise effective amounts of L-carnitine, acetyl-L-carnitine and propionyl L-carnitine are also particularly useful for treating patients with anoxia, including myocardial anoxia and cerebellar anoxia, among others. Compositions which comprise ubiquinol and alpha lipoic acid (thioctic acid) are particularly useful for influencing glucose metabolism and treating diabetes, as well as enhancing a patient's immune response as well as reducing inflammation. Compositions according to the present invention which include omega-3 fatty acids are especially useful in treating coronary disease as well as substantially reducing the risk that a patient at risk will suffer a first or subsequently heart attack. In addition, such compositions are useful in down regulating triglycerides in the blood. Compositions according to the present invention which include tocotrienols and/or tocopherols are useful for reducing cholesterol levels in patients and treating patients with heart disease including those patients at risk for suffering a first or subsequent heart attack or who are at risk of having a stroke.

Compositions according to the present invention are particularly effective because the ubiquinol is presented in a form which promotes exceptionally high bioavailability, thus producing excellent pharmacokinetics with more agent being delivered to the active site within the patient.

It is an unexpected result that formulations comprising ubiquinol in soft or hard gel capsules, when administered to patients, exhibit a bioavailability of ubiquinol which is substantially greater than when ubiquinone is administered in oral dosage form, preferably soft gel capsule form. Thus, the present compositions also represent a method for substantially enhancing the bioavailability of Coenzyme $Q_{10}$ in the patient's blood stream of an orally administrable form of ubiquinol. The enhanced bioavailability of compositions according to the present invention translates into effective treatments for numerous disease states, conditions or ailments including, for example, those conditions or disease states which are associated with oxidative tissue damage or mitochondrial dysfunction, including anoxia, reduced mitochondrial oxidative function, mitochondrial encephalomyolopathies, cardiomyopathies, heart disease, especially including congestive heart failure, ischemia/reperfusion tissue damage, neurodegenerative disorders, including Alzheimer's disease, dementia and Parkinson's disease, high blood pressure, periodontal disease, a weakened immune system and high cholesterol or high triglycerides, among numerous others. In certain preferred embodiments, compositions according to the present invention may include additional therapeutic agents, for example, statin drugs, L-carnitine, acetyl-L-carnitine and propionyl L-carnitine, omega-3 fatty acids or tocotrienols and/or tocopherols which are especially useful for treating individuals with heart disease and for reducing the likelihood that a patient at risk will suffer a first or subsequent heart attack.

In addition to oral dosage forms of ubiquinol, the present invention also contemplates compositions which may be used as topically administered creams or lotions for the treatment of wrinkles and other conditions of the skin (dermal conditions) where coenzyme Q exhibits an effect, suppositories for rectal or vaginal administration of ubiquinol, lozenges, gum, mouth rinse and toothpaste formulations, the gum and toothpaste forms especially for use in treating and/or preventing periodontal disease.

DETAILED DESCRIPTION OF THE INVENTION

The term "coenzyme Q" or "ubiquinone" is used throughout the present specification to describe a group of lipid soluble benzoquinones involved in electron transport in mitochondrial preparations, i.e., in the oxidation of succinate or reduced nicotine adenine dinucleotide (NADH) via the cytochrome system. According to the existing dual system of nomenclature, the compounds can be described as: coenzyme $Q_n$, where n is 1-12 or ubiquinone (x) in which x designates the total number of carbon atoms in the side chain and can be any multiple of 5. Differences in properties are due to the difference in the chain length. The preferred ubiquinone for use in the present invention is the reduced form of coenzyme $Q_{10}$ or ubiquinol.

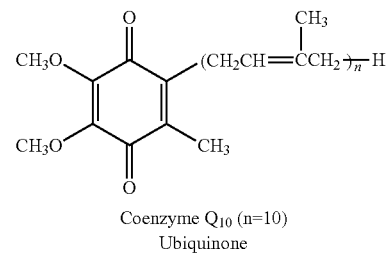

Coenzyme $Q_{10}$ (n=10)
Ubiquinone

The term "ubiquinol" is used throughout the specification to describe the reduced form of coenzyme Q which is used as the active ubiquinone in compositions according to the present invention. In ubiquinol, the quinone ring of coenzyme Q is reduced such that the structure of the compound appears as set forth below. In ubiquinol, n is preferably 10 and is derived from coenzyme $Q_{10}$. The amount of ubiquinol which is included in compositions according to the present invention ranges from about 0.1% to about 50% by weight of the final composition which is encapsulated in a soft gelatin capsule, more preferably about 0.5% to about 10% by weight, even more preferably about 1% to about 5% by weight. The amount of ubiquinol which is included in compositions to be encapsulated ranges from about 0.1 to about 10.0 times, more preferably about 1 to about 3 times the amount (in weight percent) of the lipid soluble reducing agent which is included in compositions according to the present invention.

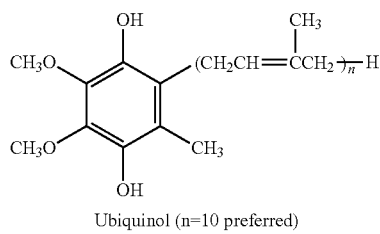

Ubiquinol (n=10 preferred)

The term "reducing agent" is used throughout the specification to describe pharmaceutically acceptable reducing agents which are added to the compositions according to the present invention in effective amounts to convert ubiquinone to ubiquinol during manufacturing and/or to substantially reduce oxidation of ubiquinol to ubiquinone (Coenzyme Q) during manufacturing and/or storage of the oral or other dosage forms of compositions according to the present invention. Preferred reducing agents include any reducing agent which is compatible with ubiquinol in pharmaceutical form and is capable of providing the requisite reducing activity to stabilize ubiquinol for storage. Preferred reducing agents for use in the present invention, include, for example, reduced glutathione, L-cysteine, N-acetyl cysteine, reduced alpha-lipoic acid (DHLA), tocotrienols, tocopherols, including vitamin E and vitamin E esters, vitamin c (ascorbate) and vitamin c esters, vitamin A (retinol, retinoic acid) and vitamin A esters, carotenoids, including alpha carotene, beta carotene, lutein, zeaxanthin, astaxanthin, lycopene, flavonoids, L-carnitine, acetyl L-carnitine, propionyl L-carnitine, magnesium, zinc, selenium, manganese, riboflavin, niacinamide, curcuminoids, proanthocyanidins from grape seed extract and pine bark extract, NADH, NADPH, resveratrol, bilberry extract, milk thistle extract and omega-3-fatty acids from for example, fish oils and marine lipid concentrate). Preferably, the reducing agent is a lipid soluble reducing agent for example, α-tocopherol (vitamin E), tocopherol esters, ascorbate esters such as ascorbyl palmitate, among others, alpha carotene and n-carotene, lycopene, flavonoids, riboflavin, curcuminoids, retinol (Vitamin A), retinoic acid, retinoic acid esters, retinol acetate, retinal and related reducing agents, preferably those which may also be used as additives in dietary supplements. While not being limited by way of theory, it is believed that the inclusion of a lipid soluble reducing agent, including lipid soluble reducings agents which are also biologically active, is preferred because such a composition provides a reducing agent which will most greatly compatibilize with the ubiquinol, resulting in reduced oxidation of the ubiquinol, thus producing greater stability. Preferred lipid soluble reducing agents are those which are also soluble in the solvents (such as a polyhydric alcohol glycerine or propylene glycol) which may be used to prepare hydrosoluble compositions comprising a reducing agent and ubiquinol. A lipid soluble reducing agent for use in the present invention comprises about 0.05% to about 25% by weight of the composition which is included in soft gelatin capsules, more preferably about 1% to about 15% by weight. The ratio of reducing agent to ubiquinol in compositions according to the present invention generally ranges from about 0.1:1 to about 10:1, more preferably about 1:5 to about 5:1, more preferably about 1:1 to about 3:1. In embodiments according to the present invention which rely on an in situ preparation of ubiquinol from ubiquinone, the amount of reducing agent which is used in the reduction reaction is preferably an excess of that amount required for the reduction reaction. The remaining reducing agent may then be incorporated into the final formulations in order to promote the storage stability of the ubiquinol.

While not being limited by way of theory, it is believed that effective concentrations of reducing agents convert substantially all ubiquinone to ubiquinol during manufacturing in an efficient method for preparing ubiquinol. In other embodiments, effective concentrations of reducing agents also prevent ubiquinol from being oxidized to ubiquinone, or alternatively reduce any ubiquinone which has been oxidized from ubiquinol during storage of the compositions according to the present invention.

The term "therapeutic reducing agent" is used to describe those reducing agents which are reducing agents for use in the present invention and which may also be used as additives in dietary supplements or alternatively, as therapeutic agents to effect or aid in producing an intended biological result.

The term "solvent" is used throughout the specification to describe a liquid into which the ubiquinol and reducing agent is at least partially solubilized, either alone or preferably in combination with a surfactant as otherwise described herein, is added. Solvents for use in the present invention include any hydrophilic solvent which is pharmaceutically acceptable and which can be used as a solvent, which alone, or in combination with surfactants as otherwise described herein, dissolves ubiquinol and the reducing agent. Preferred solvents for use in the present invention include ethanol and "polyhydric alcohols" a term which is used throughout the present invention to describe any one or more pharmaceutically compatible polyhydric alcohol compounds which are used to solubilize ubiquinol and the reducing agent used in compositions according to the present invention. Polyhydric alcohols which may be used in the present invention include, for example, glycerin (glycerol), propylene glycol and mixtures, thereof. The amount of solvent which is used in the present compositions ranges from about 0.25% to about 50% by weight, preferably about 1% to about 25% by weight, even more preferably about 1.5% to about 15-20% by weight.

The term "surfactant" or "emulsifier" is used interchangeably to describe preferred additives to compositions according to the present invention. Surfactants are solubilizers which are used to promote the solubility of the ubiquinol and the reducing agent in the polyhydric alcohol. These may be used alone or in combination with a solvent and/or a vegetable oil. The amount of surfactant used in the present invention ranges from about 0.1% to about 95% by weight, more preferably about 1.5% to about 95%, preferably about 5% to about 90% by weight. Surfactants for use in the present invention are pharmaceutically acceptable and include, for example, complex esters or ester-ethers prepared from hexahydric alcohols, alkylene oxides and fatty acids. Surfactants which exist in the liquid state at temperatures at or less than formulation temperature (generally, about 80° C. or less, more preferably about 50-60°) are preferred because they can also function as co-solvents or co-solubilizers in the present compositions. Exemplary surfactants include Span™ surfactants and Tween™ (polysorbate) surfactants, which are well-known in the art for use as stabilizers, surfactants, emulsifiers and thickeners in foods, cosmetics and medical products, among others. Preferred surfactants are those which are in a liquid state during formulation such that the surfactant may also function as a solubilizer (i.e., it has solvent-like properties). A mixture of surfactants, including a mixture of Span™ and Tween™ surfactants, most preferably, Span™ 80 and Tween™ 80, is preferred for use in the present invention.

The Span™ surfactants are partial esters of common fatty acids, such as lauric acid, palmitic acid, stearic acid and oleic acids and hexitol anhydrides such as hexitans and hexides, derived from sorbitol (see below). In the case of Span 20, the sorbitan fatty ester is based upon laurate ester. In the case of Span 60, the ester is based upon stearate ester and in the case of Span 80, the ester is based upon oleic ester. The hydrophilic character of the Span™ surfactants is supplied by free hydroxyl and oxyethylene groups, while the lipophilic character is provided by the long chain fatty groups. The Span™ surfactants tend to be oil soluble and dispersible or insoluble in water. However, these surfactants work in tandem with the more water soluble polyhydric alcohol to provide a soluble ubiquinol for soft gel formulations according to the present invention. The use of Span 80 in formulating compositions according to the present invention is preferred.

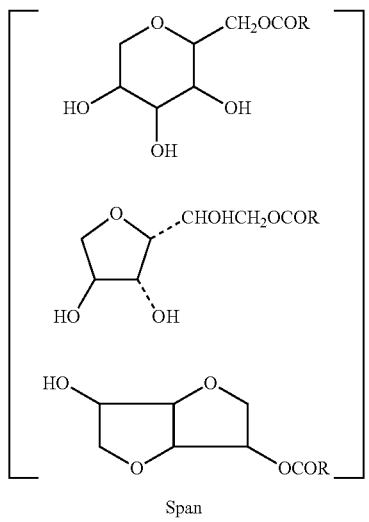

Span

R = Fatty acid residues

The Tween™ or polysorbate type surfactants are oleate esters of sorbitol and its anhydrides copolymerized with a number of moles of ethylene oxide per mole of sorbitol and sorbitol anhydride. The Tween™ or polysorbate type surfactants are derived from Span™ materials by polymerizing polyoxyethylene groups onto the nonesterified alcohols. The Tween™ surfactants are soluble or well dispersible in water. Preferred Tween™ surfactants include a sorbitan mono-9-octadecenoate poly(oxy-1,2-etheandiyl) derivative otherwise known as Tween™ 80 or Polysorbate 80.

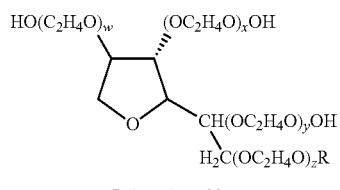

Polysorbate 80

The sum of w, x, y and z is 20 and R=$C_{17}H_{33}CO$

The term "triglycerides" or "vegetable oil" is used throughout the specification to describe an additive in compositions according to the present invention which may serve as a solubilizer or a compatibilizer. This term is used as it is used by those of ordinary skill in the art, wherein fatty acids are esterifed at the free hydroxyl positions of glycerine, producing triglycerides, which are also the primary component of vegetable oils. Preferred triglycerides for use in the present compositions include vegetable oils including "medium chain triglycerides", which are tri-fatty esters of glycerol wherein the chain length of the fatty acids range from about 10-18 carbon units. These triglycerides are used as solubilizers, diluents and excipients, to compatabilize the formulations and promote uniformity. Triglycerides are generally avoided when formulating compositions according to the present invention wherein the compositions are to be used to effect a lowering of triglycerides in the blood of a patient, especially where ubiquinol is used in combination with tocotrienols and/or tocopherols.

Vegetable oils for use in the present invention may include, for example, triglycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from vegetables, seeds or nuts and include, for example, soybean, sunflower, safflower and cottonseed oil; non-drying oils, for example castor and coconut oil; and other oils, such as, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other pharmaceutically acceptable triglyceride.

Phosphoglycerides, generally related to triglycerides in that they contain two fatty acid residues and a phosphate ester (generally, a diester) group off of the three hydroxyl groups of glycerine may also be added, alone or in combination with the triglycerides to help compatabilize or solubilize the reducing agent and/or the ubiquinone and/or ubiquinol. The phosphoglycerides may be added for their intrinsic dietary supplement value (for building muscle and nerve tissue, among other functions). These compounds may be included in compositions according to the present invention in amounts ranging from about 0.25% to about 60% by weight, preferably about 0.5% to about 35% by weight.

The term "storage" is used to describe compositions according to the present invention whereby the amount of ubiquinol in a composition after a storage period is at least about 90% by weight the total amount of ubiquinones (which includes ubiquinol and ubiquinone or coenzyme $Q_{10}$) within the composition. A storage period for purposes of the present invention is at least about one day to one week, preferably at least about 30 days (about 1 month), more preferably at least about 2 months, even more preferably at least about 6 months and even more preferably at least about 1 year or, in certain cases, even longer.

The term "patient" or "subject" is used throughout the specification to describe an animal, in most instances a human, to whom administration of the compositions according to the present invention is provided.

The term "effective amount" is used throughout the specification to describe concentrations or amounts of compounds according to the present invention which may be used to produce a favorable result, whether that result relates to a composition's therapeutic or physiological effect or its ability to function as a reducing agent to convert ubiquinone to ubiquinol during manufacturing or to prevent and/or limit the change in or oxidation of the ubiquinol or to function as a solvent in compositions according to the present invention.

The term "hydrosoluble" is used throughout the specification to describe preferred compositions according to the present invention which are encapsulated in a hard or soft, preferably a soft gelatin capsule for oral administration to a patient or subject. The term hydrosoluble is used to indicate the fact that the contents of the gelatin capsule, preferably a soft gelatin capsule, are in a form which provides effective, rapid dissolution of the contents of the gelatin capsule in the gastric juices after the gelatin capsule dissolves in the patient's gastrointestinal tract.

The term "elevated temperature" is used throughout the specification to describe a temperature above ambient temperature and generally within a range of about 40° C. to about 80° C., preferably about 45-50° C. to about 55-60° C.

The term "substantially ubiquinone-free" is used throughout the specification to describe a composition which contains ubiquinol and little or no ubiquinone. A substantially ubiquinone-free composition according to the present invention is a composition which contains ubiquinol and ubiquinone in a weight ratio of no less than 9:1, preferably no less than 19:1, even more preferably no less than 99:1. In certain preferred embodiments according to the present invention which are "ubiquinone-free", virtually no ubiquinone can be found in the ubiquinol used.

The present invention is directed to a composition comprising an effective amount of ubiquinol in combination with a reducing agent in an amount effective to substantially prevent oxidation of ubiquinol to ubiquinone and at least one surfactant or a vegetable oil (triglyceride), in an amount effective to solubilize the ubiquinol and said reducing agent, preferably in a hydrosoluble form. The composition is then formulated in oral dosage form, preferably in a soft gelatin capsule. Alternatively, in preferred dermal formulations, the compositions may be formulated for use in creams and lotions to treat conditions of the skin such as wrinkles and suppositories for rectal and/or vaginal delivery of coenzyme Q. In the case of lozenges, gum, mouth rinse and toothpaste, these formulations are preferably used for the treatment of periodontal and related gum diseases.

In the present invention, the surfactant, where used, preferably comprises about 0.1% to about 95% by weight, preferably about 1% to about 95% by weight of the composition, more preferably about 5% to about 80% by weight, even more preferably about 10% to about 75% by weight. The surfactant for use in the present invention is preferably a Tween™ surfactant or a Span™ surfactant, preferably a mixture of a Tween™ surfactant and a Span™ surfactant in a weight ratio range of about 30:1 to 2:1, more preferably about 15:1 to about 5:1, even more preferably about 13:1 to about 5:1. Preferably, a mixture of Tween™ 80 and Span™ 80 is used, optionally in combination with a solvent. While these weight ratios will serve to guide the relative amount and ratio of Tween™ surfactant and Span™ Surfactant to be included in compositions according to the present invention, one of ordinary skill will be able to readily adjust this ratio to accommodate the ubiquinol and the reducing agent in a compatible formula recognizing that the Span™ surfactants tend to be more oil soluble and the Tween™ surfactants tend to be more water soluble or dispersible. This information shall serve to guide the person of ordinary skill in formulating compositions according to the present invention, especially those formulations which do not make use of a lipid soluble reducing agent, but one which is more readily water/hydrophilic solvent soluble.

The amount of triglyceride or vegetable oil which optionally may be used in the present invention may range from about 0.1% to about 99%, more preferably about 5% to about 5% to about 90%, more preferably about 10% to about 85%, even more preferably about 15% to about 75%. The amount of triglyceride included in compositions according to the present invention will depend upon the desired characteristics which are contributed by the triglyceride to the final composition. For example, where the triglyceride is to be used in an amount effective to solubilize the ubiquinol and lipid soluble reducing agent, the amount of triglyceride utilized may be relatively high within the proposed range, because there may be no need to include one or more surfactants and/or solvents according to the present invention. However, surfactants and/or solvents may optionally be added to such formulations. Where surfactants and optionally, solvents are added to the compositions according to the present invention, the amount of triglyceride which may be added to the composition may vary at the lower end of the range as set forth above, especially where the reducing agent is more hydrophilic in nature. Phosphoglycerides may also be added to enhance the effect of the triglycerides in solubilizing and/or compatabilizing the ubiquinol and/or the reducing agent. These phosphoglycerides may also be added for their benefit as dietary supplements.

Compositions according to the present invention are preferably formulated in oral dosage form, even more preferably in hard or soft gelatin capsules, more preferably soft gelatin capsules, as the oral dosage form. The gelatin capsule is generally taken by the subject orally. It is an unexpected result that the ubiquinol from the soft gelatin oral dosage form results in a significantly enhanced bioavailability of ubiquinol (which is in equilibrium with ubiquinone within the patient) compared to similar compositions which contain ubiquinone alone.

Alternatively, in certain preferred formulations, the compositions may be formulated for use in creams and lotions to treat conditions of the skin such as wrinkles and suppositories for rectal and/or vaginal delivery of coenzyme Q. In the case of lozenges, gum, mouth rinse and toothpaste, these formulations may be used generally for systemic delivery of coenzyme Q or locally, primarily for the treatment of periodontal and related gum diseases.

Compositions according to the present invention may also include a pharmaceutically acceptable carrier, excipient or additive. Care must be taken to avoid having any one or more of these optional ingredients impact the solubility characteristics of the ubiquinol and reducing agent in the surfactant and/or vegetable oil.

Although ubiquinol can be produced as a first step and then added to the other components in making oral dosage forms according to the present invention, the preferred method is to provide for the in situ preparation of ubiquinol from the less expensive and commercially available ubiquinone (ubiquinol is not commercially available. In a preferred method of making compositions according to the present invention from coenzyme Q as the starting material, the components other than the coenzyme Q and, in certain cases, the reducing agent are added together at elevated temperature (generally, at a temperature of about 45-80° C., preferably at a temperature of about 50-60° C.) until the components are thoroughly mixed.

At the point of thorough mixing at elevated temperature, the components are in a liquid state. Subsequent to mixing of the components, coenzyme $Q_{10}$ is added to the mixture at elevated temperature as described above and thoroughly mixed into the liquid components for a sufficient period. If the mixture to which the coenzyme Q is added contains an effective concentration of reducing agent, coenzyme Q will be converted to ubiquinol and the mixture can be used to provide oral dosage forms, preferably hard or soft gelatin capsules, even more preferably soft gelatin capsules. In preferred embodiments, after the coenzyme $Q_{10}$ is added, a reducing agent is thereafter added in an amount effective to convert the coenzyme Q to ubiquinol or alternatively, in an amount which not only is effective to convert coenzyme Q to ubiquinol, but also effective to maintain ubiquinol in its reduced state.

The solubilized composition containing ubiquinol, a reducing agent and a surfactant, a vegetable oil or both, in its preferred liquid form is water-free and therefore, suitable for use in oral dosage form, preferably, in gelatin capsules, which are prepared by conventional means as those skilled in the art would readily recognize. In preferred embodiments according to the present invention soft gelatin capsules are used, although two-piece hard gelatin capsules may be used (especially where the liquid composition at elevated temperature solidifies at room temperature). Hard gelatin capsules for use in the present invention are those which are well known in the art and comprise gelatin or hydroxypropylmethyl cellulose or a related cellulosic material in combination with glycerin. Any other acceptable formula which is well known in the art may also be used to provide two piece hard gelatin capsules. Soft gelatin capsules may comprise, for example, gelatin, glycerin and sorbitol as well as other components which are well known in the art. The gelatin capsules are generally tasteless, easy to swallow and they readily dissolve in the gastric juices of the digestive tract.

Alternatively, the compositions according to the present invention may be provided in tablet form using conventional tabletting methods well known in the art, for example, by adsorbing the composition onto a suitable solid carrier or excipient. The compositions according to the present invention can also be provided in a microencapsulated free flowing form. Enteric coated capsules or tablets are also contemplated by the present invention in order to enhance delivery of ubiquinol from the upper gastrointestinal tract (primarily, the duodenum where most of the absorption occurs). Enteric coating capsules may be produced by coating a tablet with composition containing, for example, hypromellose phthalate, diethyl phthalate, polyethylene glycol or any other suitable composition containing pharmaceutically acceptable enteric coating ingredients. One of ordinary skill using standard pharmaceutical formulation and packaging practices will be able to readily prepare any one or more of the oral dosage forms according to the present invention.

Alternatively, in certain preferred formulations, the compositions may be formulated for use in creams and lotions to treat conditions of the skin such as wrinkles using standard cosmetic and personal care product formulation techniques. In the case of suppositories, compositions according to the present invention may be used in combination with an effective amount of a thickening agent to produce a formulation in suppository delivery form for rectal and/or vaginal delivery of delivery of coenzyme Q. In the case of lozenges, gum, mouth rinse and toothpaste, these formulations are produced preferably to be used for the treatment of periodontal and related gum diseases. In each instance where particular formulation is to be used, standard formulary processes and additives may be used to produce the desired dosage form. The requisite types and amounts of additives, such as thickeners, additional surfactants and/or solvents, flavors, coloring agents, emollients, humectants, fillers, and additional biologically active compounds (such as anti-caries agents and the like), etc. will be used in combination with a base formulation to produce the desired final products.

The concentration of ubiquinol in the compositions according to the present invention will depend on absorption, distribution, inactivation, and excretion rates of the ubiquinol and its metabolites as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient, ubiquinol, may be administered at once, or may be divided into a number of smaller doses to be administered at varying intervals of time.

The active compound of the present invention can also be mixed with other active materials that do not impair the desired action, or with materials that supplement the desired action provided that the added materials do not change the activity of the included compounds.

Administration of the active may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets, as an alternative to soft or hard gelatin capsules, may also be used to enhance bioavailability of the compounds from an oral route of administration. The most effective dosage form will depend upon the pharmacokinetics of the particular agent chosen as well as the severity of the condition in the patient to be treated. Oral dosage forms are particularly preferred, because of ease of administration and prospective favorable patient compliance. Creams and lotions are preferred where skin conditions, especially wrinkles, are to be treated. Lozenges, gums, mouth rinse and toothpaste are preferred where periodontal disease and other conditions of the patient's gums are to be treated.

To prepare the pharmaceutical compositions according to the present invention, an effective amount of ubiquinol in combination with a reducing agent and a surfactant or a vegetable oil is formulated in gelatin capsules (hard or soft), or in alternative embodiments, is intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. For solid oral preparations such as powders, tablets, capsules, and for solid preparations such as suppositories, suitable carriers and additives including cyclodestrins, starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may further increase the bioavailability of the compounds in the patient.

Liposomal suspensions (including liposomes targeted to viral antigens) may also be prepared by conventional methods to produce pharmaceutically acceptable carriers, especially for parenteral delivery. This may be appropriate for the delivery of free nucleosides, acyl nucleosides or phosphate ester pro-drug forms of the nucleoside compounds according to the present invention.

Having generally described the invention, reference is now made to the following examples which are intended to illustrate preferred embodiments and comparisons. The included examples are not to be construed as limiting the scope of this invention as is more broadly set forth above and in the appended claims.

Example 1

Oral Dosage Form of Ubiquinol w/Surfactants

This example sets forth a composition and method for providing a soft gelatin capsule which relies on the reduction of ubiquinone to ubiquinol utilizing lipid soluble reducing agents and the stabilization of the resulting hydroxoluble reduced form in a soft gelatin capsule.
Procedure:
Mix the following components in a suitable jacketed mixing vessel:
Span 80 (1-15%);
Glycerine, propylene glycol or other suitable polyhydric alcohol (1%-15%);
Tween80 (20% to 90%);
Medium Chain Triglycerides (MCT, 5% to 25%).

After mixing the above components, the mixture is raised in temperature to about 55° C. (±5°) while mixing constantly. 0.5% to about 10% of Coenzyme Q is then added to the above heated mix while stirring. The coenzyme Q is thoroughly mixed into solution at elevated temperature for a period of from 1-2 hours. Then ascorbyl palmitate (or another suitable reducing agent) is added in an effective amount ranging from about 1% to about 15% by weight and the mixture at elevated temperature is stirred for 1 to 2 hours or at least until the mixture is a crystal clear bright orange—indicating that the reduction of ubiquinone to ubiquinol is complete. The mixing vessel is then connected to a cooling system (cooled water) and while mixing, the heated mixture is cooled to room temperature (about 23° C.±3°). After the liquid is cooled to room temperature, the mixer is shut down and the cooling water is disconnected. The liquid is then transferred to a suitable stainless steel drum and the empty space in the drum is flushed with nitrogen. The drum is then sealed. The finished liquid is analyzed using HPLC using an electrochemical detector for quantitative determination of ubiquinone and ubiquinol. The liquid is thereafter encapsulated in soft gelatin capsules containing an opacifier ($TiO_2$) and colorant utilizing standard manufacturing procedures.

The final gelatin capsule has the following components (in percent by weight excluding gelatin capsule):

| | |
|---|---|
| Span 80 | 5% |
| Glycerine | 4% |
| Tween 80 | 65% |
| MCT | 18% |
| $CoQ_{10}$ | 4% |
| Ascorbyl Palmitate | 4% |

Example II

Alternative Method

This example sets forth a composition and method for providing a soft gelatin capsule which relies on the reduction of ubiquinone to ubiquinol utilizing lipid soluble reducing agents and the stabilization of the resulting hydrosoluble reduced form in a soft gelatin capsule using vegetable oil.
Procedure:
Mix the following components in a suitable jacketed mixing vessel:
Vitamin E acetate (2-20%);
Hydroxylated lecithin (2%-20%);
Phosphatidyl chloline solution (20% to 50%);
Medium Chain Triglycerides, other suitable vegetable oil (5% to 40%).
Gelucire (5% to 50%).

After mixing the above components, the mixture is raised in temperature to about 55° C. (±5°) while mixing constantly. 0.5% to about 10% of Coenzyme Q is then added to the above heated mix while stirring. The coenzyme Q is thoroughly mixed into solution at elevated temperature for a period of about 1 hour. Then ascorbyl palmitate (or another suitable reducing agent) is added in an effective amount ranging from about 1% to about 10% by weight and the mixture at elevated temperature is stirred for 1 to 2 hours or at least until the mixture is a clear solution—indicating that the reduction of ubiquinone to ubiquinol is complete. The mixing vessel is then connected to a cooling system (cooled water) and while mixing, the heated mixture is cooled to room temperature as in example 1. After the liquid is cooled to room temperature, the mixer is shut down and the liquid is then transferred to a suitable stainless steel drum and the empty space in the drum is flushed with nitrogen. The drum is then sealed. The finished liquid is analyzed as in example 1 and thereafter encapsulated in soft gelatin capsules containing an opacifier ($TiO_2$) and colorant utilizing standard manufacturing procedures.

The final gelatin capsule has the following components (in percent by weight excluding gelatin capsule):

| | |
|---|---|
| Vitamine E acetate | 6% |
| Hydroxylated Lecithin | 4% |
| Phosphatiyl Choline Solution (52%) | 32% |
| MCT | 20% |
| Gelucire | 30% |
| $CoQ_{10}$ | 4% |
| Ascorbyl Palmitate | 4% |

Example III

Ubiquinol and Rice Bran or Palm Oil Concentrate Containing Tocotrienols and Tocopherols This example is directed to the preparation of a stable formulation of a hydrosoluble reduced form (ubiquinol) of Coenzyme Q10 with a Rice Bran or Palm Oil concentration containing tocotrienols and tocopherols.
Procedure: mix Tween 80, Span 80, glycerin and palm oil or rice bran oil concentrate in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then ascorbyl palmitate (or another suitable reducing agent) is added in an effective amount ranging from about 0.1% to about 10% by weight and the mixture at elevated temperature is stirred for 1 to 2 hours or at least until the mixture is a crystal clear bright orange—indicating that the reduction of ubiquinone to ubiquinol is complete. Alternatively, the palm oil concentrate or rice bran oil concentrate may be added after the initial reduction reaction takes place. After mixing is completed, the mixing vessel is then connected to a cooling system (cooled water) and while mixing, the heated mixture is cooled to room temperature (about 23° C.±3°). After the liquid is cooled to room temperature, the mixer is shut down and the cooling water is disconnected. The liquid is then transferred to a suitable stainless steel drum and the empty space in the drum is flushed with nitrogen. The drum is then sealed. The finished liquid is analyzed using HPLC using an electrochemical detector for quantitative determination of ubiquinone and ubiquinol. The liquid is thereafter encapsulated in soft gelkin capsules containing an opacifier (TiO$_2$) and colorant utilizing standard manufacturing procedures. Alternatively, the liquid may be encapsulated in a two piece hard gelatin capsule.

The final gelatin capsule has the following components (in percent by weight excluding gelatin capsule):

| Range | Typical Tx | Wt. Percent |
|---|---|---|
| (0.1%-10%) | Coenzyme Q10 | 3.33% |
| (10%-50%) | Tween 80 | 70.74% |
| (0.5%-15%) | Span 80 | 5.09% |
| (0.1%-10%) | Ascorbyl Palmitate | 3.63% |
| (0.1%-10%) | Glycerin | 3.55% |
| (10%-90%) | Palm Oil Concentrate or Rice Bran | 13.65% |
| | Oil Concentrate (source of mixed tocotrienols and tocopherols) | 100.00% |

Advantages
1. The use of ubiquinol improves bioavailability of Coenzyme Q10.
2. Reduced form of Coenzyme Q10 provides an active, antioxidant form of CoQ10.
3. Inclusion of tocotrienols and tocopherols are naturally derived from Palm Oil or Rice Bran Oil.
4. Combination of CoQ10 and tocotrienols/tocopherols is particularly useful in reducing elevated cholesterol levels.

Example IV

Ubiquinol with Omega-3 Fatty Acids and Docosahexaenoic Acid (DHA) from Fish Body Oil Concentrate and/or Flaxseed Oil and/or Algae This example is directed to the preparation of a stable formulation of a hydrosoluble reduced form (ubiquinol) of Coenzyme Q10 with Omega-3 Fatty Acids from fish body oil and/or flaxseed oil and/or algae.

Procedure: mix Tween 80, Span 80, glycerin or propylene glycol, medium chain triglycerides and fish oil concentrate in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then ascorbyl palmitate and vitamin E acetate (or vitamin e or mixed tocopherols or another suitable reducing agent) is added and the mixture at elevated temperature is stirred for 1 to 2 hours or at least until the mixture is a crystal clear bright orange—indicating that the reduction of ubiquinone to ubiquinol is complete. Alternatively, the fish oil concentrate, flaxseed oil or algae derived omega-3-fatty acids may be added after the initial reduction reaction takes place. After mixing is completed, the mixing vessel is then connected to a cooling system (cooled water) and while mixing, the heated mixture is cooled to room temperature (about 23° C.±3°). After the liquid is cooled to room temperature, the mixer is shut down and the cooling water is disconnected. The liquid is then transferred to a suitable stainless steel drum and the empty space in the drum is flushed with nitrogen. The drum is then sealed. The finished liquid is analyzed using HPLC using an electrochemical detector for quantitative determination of ubiquinone and ubiquinol. The liquid is thereafter encapsulated in soft gelatin capsules containing an opacifier (TiO$_2$) and colorant utilizing standard manufacturing procedures. Alternatively, the liquid may be encapsulated in a two piece hard gelatin capsule.

The final gelatin capsule has the following components (in percent by weight excluding gelatin capsule):

| Range | Typical Tx | Wt. Percent |
|---|---|---|
| (0.1%-10%) | Coenzyme Q10 | 1.53% |
| (5%-50%) | Tween 80 | 30.64% |
| (0.5%-15%) | Span 80 | 2.34% |
| (0.1-25%) | Vitamin E Acetate | 1.22% |
| (0.1%-10%) | Ascorbyl Palmitate | 1.53% |
| (0.1%-25%) | Medium Chain Triglycerides | 5.35% |
| (0.1%-10%) | Glycerin or Propylene Glycol | 1.63% |
| (10%-90%) | Fish Oil Concentrate | 55.75% |
| | (Rich in Omega-3 fatty acids) | 100.00% |

Advantages
1. The use of ubiquinol improves bioavailability of Coenzyme Q10.
2. Reduced form of Coenzyme Q10 provides an active, antioxidant form of CoQ10.
3. Inclusion of fish oil concentrate/flaxseed oil and/or DHA (algae derived) in dosage form
Providing improved bioavailability.
4. Combination of CoQ10 and omega-3 fatty acids capable of Treating cardiomyopathies, high blood pressure, with combined reduction
In levels of triglycerides in the blood.

Example V

Ubiquinol Intensive Anti-Wrinkle Soft Cream with Alpha-Hydroxy Acids

Active Ingredient: Ubidecarenone (Coenzyme Q$_{10}$)
Base Ingredients: Sorbitan Monooleate NF
 Glycerin USP
 Polysorbate 80 NF
 D-Alpha Tocopherol Conc. F.C.C.
 Ascorbyl palmitate (% ascorbyl palmitate≥% of ubiquinone in sample)
 Medium Chain Triglycerides
 IMWITOR 370 (Glyceryl Stearate Citrate)
 MIGLYOL 812 (Caprylic/Capric Triglyceride)
 SOFTISAN 601 (Glycerol Cocoate and Hydrogenated Coconut Oil and Ceteareth-25)

EWALAN ODE-50 (Octyldodecyl Lanolaet)
Pronalen Fuir Acid AHA-5 (Lemon and Passion Fruit Concentrate)
Preservative
Purified Water
Perfume Exemplary Procedure: mix sorbitan monooleate NF, polysorbate 80 NF, glycerin and medium chain triglycerides in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the alpha tocopherol and ascorbyl palmitate (or other suitable reducing agent) are added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature in order to ensure a uniform product. The product (a cream) may be packaged using standard packaging procedures.

Example VI

Ubiquinol Suppository Formula (Rectal/Vaginal)

Active Ingredient: Ubidecarenone (Coenzyme $Q_{10}$)
Base Ingredients: Covitol F 1000
  Ascorbyl Palmitate
  Span 80 NF
  Tween 80 NF
  Glycerin USP
  Medium Chain Triglycerides
  Softisan 378
  Softisan 100

Exemplary Procedure: mix Span 80 and Tween 80, glycerin and medium chain triglycerides in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the ascorbyl palmitate (or other suitable reducing agent) is added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature in order to ensure a uniform product. The thoroughly mixed product may be formed into suppositories using standard procedures.

Example VII

Ubiquinol Suppository Formula (Rectal/Vaginal)

Active Ingredient: Ubidecarenone (Coenzyme $Q_{10}$)
Base Ingredients: Covitol F 1000
  Ascorbyl Palmitate
  Span 80 NF
  Tween 80 NF
  Glycerin USP
  Medium Chain Triglycerides
  WITEPSOL H-32

Exemplary Procedure: mix Span 80 and Tween 80, glycerin and medium chain triglycerides in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the ascorbyl palmitate (or other suitable reducing agent) is added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature in order to ensure a uniform product. The thoroughly mixed product may be formed into suppositories using standard procedures.

Example VIII

Ubiquinol Toothpaste

Active Ingredient: Ubidecarenone (Coenzyme $Q_{10}$)
Base Ingredients: Sorbitan Monooleate NF
  Glycerin USP
  Polysorbate 80 NF
  D-Alpha Tocopherol Conc. F.C.C.
  Ascorbyl palmitate (wt. % ascorbyl palmitate.≥% of ubiquinone)
  Medium Chain Triglycerides
  Purified Water
  Hydrated Silica
  Sorbitol
  Tetrapotassium Pyrophosphate
  PEG-6
  Disodium Pyrophosphate
  Tetrasodium Pyrophosphate
  Sodium Lauryl Sulfate
  Flavor
  Xanthan Gum
  Sodium Saccharin
  Carbomer 956
  FD & C No. 1

Exemplary Procedure: mix Sorbitan Monooleate and Polysorbate 80, glycerin and medium chain triglycerides in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the alpha tocopherol and ascorbyl palmitate (or other suitable reducing agent) are added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature (thickeners to be added last to provide paste-like viscosity) in order to ensure a uniform toothpaste product. The thoroughly mixed product may be packaged in tubes using standard procedures.

Example IX

Ubiquinol Toothpaste Alternative 1

Active Ingredient: Ubidecarenone (Coenzyme $Q_{10}$)
Base Ingredients: Sorbitan Monooleate NF
  Glycerin USP
  Polysorbate 80 NF
  D-Alpha Tocopherol Conc. F.C.C.

Ascorbyl palmitate (wt. % ascorbyl palmitate≥wt. % ubiquinone)
Medium Chain Triglycerides
Purified Water
Calcium Carbonate
Calcium Carageenan
Cellulose Gum
Sorbitol
PEG-8
Hydrated Silica
Sodium Lauryl Sulfate
Flavor
Sodium Saccharin
Sorbitol
Sodium Benzoate
D & C Red #30 Lake
Yellow #10 Lake
FD & C Blue #1 Lake
Flavor
Titanium Dioxide Exemplary Procedure: mix Sorbitan Monooleate and Polysorbate 80, glycerin and medium chain triglycerides in a suitable jacketed mixing vessel. After mixing the above components, +− the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the alpha tocopherol and ascorbyl palmitate (or other suitable reducing agent) are added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature (thickeners to be added last to provide paste-like viscosity) in order to ensure a uniform toothpaste product. The thoroughly mixed product may be packaged in tubes using standard procedures.

Example X

Ubiquinol Toothpaste Alternative 2

Active Ingredient: Ubidecarenone (Coenzyme $Q_{10}$)
Base Ingredients: Sorbitan Monooleate NF
Glycerin USP
Polysorbate 80 NF
D-Alpha Tocopherol Conc. F.C.C.
Ascorbyl palmitate (wt. % ascorbyl palmitate≥wt. % ubiquinone)
Medium Chain Triglycerides
Purified Water
Dicalcium Phosphate Dihydrate
Sorbitol
Tetrasodium Pyrophosphate
Sodium Lauryl Sulfate
Flavor
Sodium Saccharin
Cellulose Gum Exemplary Procedure: mix Sorbitan Monooleate and Polysorbate 80, glycerin and medium chain triglycerides in a suitable jacketed mixing vessel. After mixing the above components, the mixture is raised in temperature to about 55° C. (±5°) while mixing constantly. 0.1% to about 10% of Coenzyme Q is then added to the above heated mix while stirring. The coenzyme Q is thoroughly mixed into solution at elevated temperature for a period of from 1-2 hours. Then the alpha tocopherol and ascorbyl palmitate (or other suitable reducing agent) are added and the mixture at elevated temperature is stirred for 1 to 2 hours or at least until the mixture is a crystal clear bright orange—indicating that the reduction of ubiquinone to ubiquinol is complete. The remaining components are added thereafter at elevated temperature (thickeners to be added last to provide paste-like viscosity) in order to ensure a uniform toothpaste product. The thoroughly mixed product may be packaged in tubes using standard procedures.

It is to be understood by those skilled in the art that the foregoing description and examples are illustrative of practicing the present invention, but are in no way limiting. Variations of the detail presented herein may be made without departing from the spirit and scope of the present invention as defined by the following claims.

The invention claimed is:

1. A composition comprising ubiquinone and an amount of an ascorbate ester reducing agent effective to reduce said ubiquinone to ubiquinol in said composition; said composition further comprising an amount of a pharmaceutically acceptable surfactant, triglyceride, phosphoglyceride, fatty ester, vegetable oil or a mixture thereof and optionally, a pharmaceutically acceptable solvent, effective to solubilize said ubiquinone, ubiquinol and said reducing agent into solution, wherein after reduction of said ubiquinone, said ubiquinol in said composition comprises more than 95% by weight of a total amount of ubiquinol and ubiquinone in said composition.

2. The composition according to claim 1 wherein said reducing agent is ascorbyl palmitate.

3. The composition according to claim 2 wherein said ubiquinone is Coenzyme $Q_{10}$.

4. The composition according to claim 3 wherein said surfactant is selected from the group consisting of complex ester or ester-ether surfactants prepared from hexahydric alcohols, alkylene oxides and fatty acids, polysorbate surfactants and mixtures thereof.

5. The composition according to claim 4 wherein said complex ester or ester-ether surfactant is a compound according to the structure:

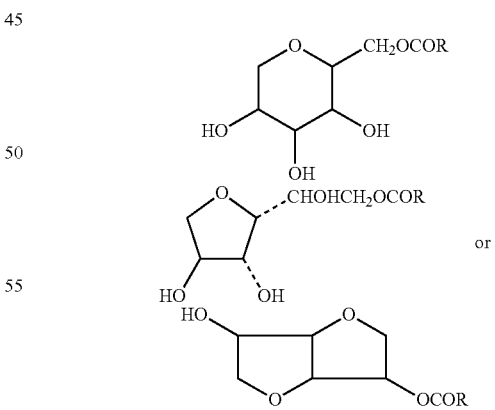

where R is a fatty acid residue.

6. The composition according to claim 5 wherein R is oleoyl.

7. The composition according to claim 3 wherein said surfactant is a polysorbate surfactant according to the structure:

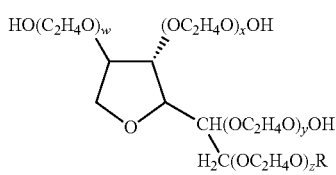

where R is an oleoyl group and the sum of w, x, y and z is 20.

8. The composition according to claim 4 wherein said surfactant is a mixture of a complex ester or ester-ether surfactant prepared from hexahydric alcohols, alkylene oxides and fatty acids and a polysorbate surfactant.

9. The composition according to claim 8 wherein said complex ester or ester-ether surfactant is a compound according to the structure:

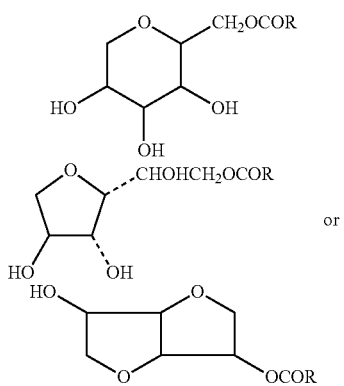

where R is a fatty acid residue.

10. The composition according to claim 8 wherein said polysorbate surfactant is a compound according to the structure:

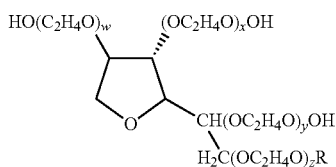

where R is an oleoyl group and the sum of w, x, y and z is 20.

11. The composition according to claim 3 wherein said triglyceride comprises medium chain triglycerides.

12. The composition according to claim 1 wherein said vegetable oil is selected from the group consisting of soybean oil, sunflower oil, safflower oil, cottonseed oil, castor oil, rapeseed oil, coconut oil, palm oil and mixtures thereof.

13. The composition according to claim 3 further comprising an effective amount of a HMG CoA reductase inhibitor drug.

14. The composition according to claim 13 wherein said inhibitor drug is selected from the group consisting of lovastatin, pravastatin, fluvastatin, simvastatin, mevastatin, fluindostatin.

15. The composition according to claim 4 further comprising an effective amount of a HMG CoA reductase inhibitor drug.

16. The composition according to claim 15 wherein said inhibitor drug is selected from the group consisting of lovastatin, pravastatin, fluvastatin, simvastatin, mevastatin, fluindostatin, atorvastatin, cerivastatin, compactin and mixtures thereof.

17. The composition according to claim 3 further comprising an omega-3 fatty acid or mixture of omega-3-fatty acids.

18. The composition according to claim 3 further comprising a reducing agent selected from the group consisting of tocotrienols, tocopherols and mixtures thereof.

19. The composition according to claim 3 further comprising a reducing agent is selected from the group consisting of L-carnitine, acetyl L-carnitine, propionyl L-carnitine and mixtures thereof.

20. The composition according to claim 3 wherein said solvent is ethanol or a polyhydric alcohol selected from the group consisting of glycerin, propylene glycol and mixtures thereof.

21. The composition according to claim 3 in oral pharmaceutical dosage form.

22. The composition according to claim 21 in topical dosage form.

23. The composition according to claim 22 which is formulated into a cream or lotion for dermal application.

24. A composition in oral dosage form comprising ubiquinol obtained from the in situ reduction of ubiquinone to ubiquinol in said composition; an amount of an ascorbate ester reducing agent effective to reduce ubiquinone to ubiquinol in said composition; and an amount of a surfactant, triglyceride, phosphoglyceride, fatty ester, vegetable oil or mixture thereof and optionally, a solvent, effective to solubilize said ubiquinone, ubiquinol and reducing agent in said composition into solution, said oral dosage form being formulated in a gelatin capsule or tablet, wherein said ubiquinol in said composition comprises more than 95% by weight of a total amount of ubiquinol and ubiquinone in said composition.

25. The composition according to claim 24 wherein said reducing agent is ascorbyl palmitate.

26. The composition according to claim 25 wherein said ubiquinone is Coenzyme $Q_{10}$.

27. The composition according to claim 26 wherein said surfactant is selected from the group consisting of complex ester or ester-ether surfactants prepared from hexahydric alcohols, alkylene oxides and fatty acids, polysorbate surfactants and mixtures thereof.

28. The composition according to claim 27 wherein said complex ester or ester-ether surfactant is a compound according to the structure:

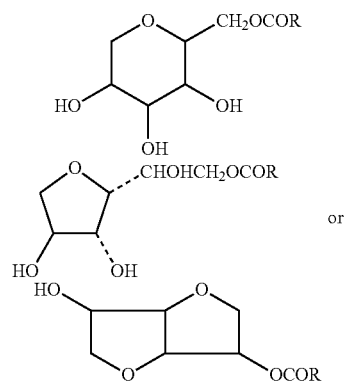

where R is a fatty acid residue.

29. The composition according to claim 28 wherein R is oleoyl.

30. The composition according to claim 27 wherein said surfactant is a polysorbate surfactant according to the structure:

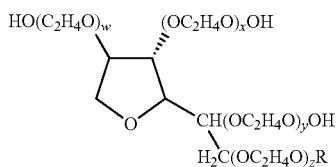

where R is oleoyl and the sum of w, x, y and z is 20.

31. The composition according to claim 26 wherein said surfactant is a mixture of a complex ester or ester-ether surfactant prepared from hexahydric alcohols, alkylene oxides and fatty acids and a polysorbate surfactant.

32. The composition according to claim 31 wherein said complex ester or ester-ether surfactant is a compound according to the structure:

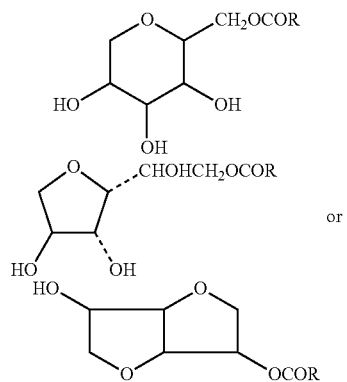

where R is a fatty acid residue.

33. The composition according to claim 31 wherein said polysorbate surfactant is a compound according to the structure:

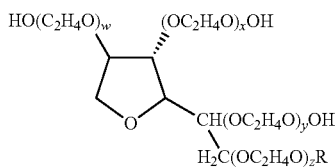

where R is an oleoyl group and the sum of w, x, y and z is 20.

34. The composition according to claim 26 wherein said triglyceride comprises medium chain triglycerides.

35. The composition according to claim 26 wherein said vegetable oil is selected from the group consisting of soybean oil, sunflower oil, safflower oil, cottonseed oil, castor oil, rapeseed oil, coconut oil, palm oil, flaxseed oil and mixtures thereof.

36. The composition according to claim 26 further comprising an effective amount of a HMG CoA reductase inhibitor drug.

37. The composition according to claim 36 wherein said inhibitor drug is selected from the group consisting of lovastatin, pravastatin, fluvastatin, simvastatin, mevastatin, fluindostatin.

38. The composition according to claim 27 further comprising an effective amount of a HMG CoA reductase inhibitor drug.

39. The composition according to claim 38 wherein said inhibitor drug is selected from the group consisting of lovastatin, pravastatin, fluvastatin, simvastatin, mevastatin, fluindostatin, atorvastatin, cerivastatin, compactin and mixtures thereof.

40. The composition according to claim 26 father including an omega-3 fatty acid or mixture of omega-3-fatty acids.

41. The composition according to claim 27 further including a reducing agent selected from the group consisting of tocotrienols, tocopherols and mixtures, thereof.

42. The composition according to claim 27 further including a reducing agent is selected from the group consisting of L-carnitine, acetyl-L-carnitine, propionyl L-carnitine and mixtures, thereof.

43. The composition according to claim 26 wherein said solvent is ethanol or a polyhydric alcohol selected from the group consisting of glycerin, propylene glycol and mixtures thereof.

44. A method for increasing the bioavailability of ubiquinone from an orally or topically administered composition comprising administering to a subject a composition comprising an effective amount of ubiquinol obtained from the in situ reduction of ubiquinone to ubiquinol in said composition in oral or topical dosage form, said composition comprising ubiquinone and an amount of ascorbyl palmitate as a reducing agent effective to reduce ubiquinone to ubiquinol; said composition further comprising an amount of a surfactant, triglyceride, phosphoglyceride, fatty ester, vegetable oil or mixture thereof effective to solubilize said ubiquinone, ubiquinol and said reducing agent in said composition into solution, wherein said ubiquinol, after reduction of ubiquinone to ubiquionol, comprises more than 95% by weight of a total amount of ubiquinol and ubiquinone in said composition, wherein said composition is storage stable, said ubiquinone is Coenzyme $Q_{10}$ and said composition further comprises an amount of a reducing agent effective to reduce or prevent the oxidation of ubiquinol to ubiquinone.

45. The composition according to claim 5 wherein R is selected from the group consisting of lauroyl, stearoyl and oleoyl.

46. The composition according to claim 9 wherein R is selected from the group consisting of lauroyl, stearoyl and oleoyl.

47. The composition according to claim 28 wherein R is selected from the group consisting of lauroyl, stearoyl and oleoyl.

48. The composition according to claim 32 wherein R is selected from the group consisting of lauroyl, stearoyl and oleoyl.

49. The composition according to claim 1 wherein said ascorbate ester is lipid soluble.

50. The composition according to claim 24 wherein said ascorbate ester is lipid soluble.

* * * * *